US011416651B2

(12) United States Patent
Roberts et al.

(10) Patent No.: US 11,416,651 B2
(45) Date of Patent: Aug. 16, 2022

(54) DYNAMICALLY ADJUSTABLE TRAINING SIMULATION

(71) Applicant: International Business Machines Corporation, Armonk, NY (US)

(72) Inventors: Melanie E. Roberts, Queensland (AU); Roslyn I. Hickson, Fitzroy North (AU); Olivia J. Smith, Melbourne (AU); Manoj Gambhir, Port Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 930 days.

(21) Appl. No.: 16/205,260

(22) Filed: Nov. 30, 2018

(65) Prior Publication Data

US 2020/0175123 A1 Jun. 4, 2020

(51) Int. Cl.
*G06F 30/20* (2020.01)
*G09G 5/08* (2006.01)
*G06F 3/01* (2006.01)
*G06N 7/00* (2006.01)
(Continued)

(52) U.S. Cl.
CPC .............. *G06F 30/20* (2020.01); *A61B 5/165* (2013.01); *G06F 3/015* (2013.01); *G06N 7/005* (2013.01); *G06N 20/00* (2019.01); *G06F 2203/011* (2013.01)

(58) Field of Classification Search
CPC .......... G06F 30/20; G06F 3/015; G06F 3/033; G06F 3/02; G06N 20/00; G06N 7/005; A61B 5/165; G09G 5/08; G09G 5/00
See application file for complete search history.

(56) References Cited

U.S. PATENT DOCUMENTS

| 9,731,184 B2 | 8/2017 | Cheng |
| 2004/0230549 A1 | 11/2004 | Freer et al. |
| 2015/0251074 A1 | 9/2015 | Ahmed et al. |

(Continued)

FOREIGN PATENT DOCUMENTS

WO 2017096104 A1 6/2017

OTHER PUBLICATIONS

Buttussi et al. "MOPET: A context-aware and user-adaptive wearable system for fitness training", Artificial Intelligence in Medicine 42.2, Feb. 1, 2008, ISSN:09333657, pp. 153-163, <https://dialog.proquest.com/professional/docview/777151034?accountid=15391>.

*Primary Examiner* — Pegeman Karimi
(74) *Attorney, Agent, or Firm* — Christopher M. Pignato

(57) ABSTRACT

Systems, methods and program products for administering and modifying a simulation that incorporates the use of biometric data collection and computer-based predictive modeling techniques to reliably identify changes in the stress level of simulation participants while predictively adapting the simulation environment to manage each participants' stress levels within a pre-set or desired range. Each participant may have their biometric data collected and continuously monitored by wearing a computing device comprising biometric sensors, camera systems and audio recording devices. As the participants biometric data changes, the system monitors the participant for changes in stress level and maintains a desired stress level in the participant by modifying the adjustable properties of one or more virtual objects or computer-accessible real physical objects of the simulation environment to increase or decrease the stress level of the simulation on participants.

17 Claims, 10 Drawing Sheets

(51) Int. Cl.
*G06N 20/00* (2019.01)
*A61B 5/16* (2006.01)

(56) References Cited

U.S. PATENT DOCUMENTS

| | | |
|---|---|---|
| 2016/0263439 A1 | 9/2016 | Ackland |
| 2016/0292373 A1 | 10/2016 | Spors et al. |
| 2017/0071524 A1 | 3/2017 | Yoo |
| 2017/0148214 A1* | 5/2017 | Muniz-Simas ........ A61B 5/165 |
| 2017/0173394 A1 | 6/2017 | Rider et al. |
| 2017/0193851 A1 | 7/2017 | McNichol et al. |
| 2017/0213474 A1* | 7/2017 | Welles ................. G09B 19/167 |
| 2017/0216671 A1 | 8/2017 | Wisbey et al. |
| 2017/0318360 A1* | 11/2017 | Tran ........................ H04Q 9/00 |

* cited by examiner

DYNAMICALLY ADJUSTABLE TRAINING SIMULATION

TECHNICAL FIELD

The present invention relates generally to the field of computer-based training simulations, and more particularly to real-time adjustments of simulation environments.

BACKGROUND

A computer simulation may be described as the usage of a computer to imitate a real-world process or system based on the behavior of another system that is modeled after real-world situations. A simulation may use a model or mathematical description of a real system, often in the form of a computer program, which may encompass specific characteristics, behaviors or other variables associated with the system being modeled. When the computer program is executed, the resulting mathematical interpretation of the simulation may output a predicted behavior analogous to a behavior expected to be exhibited by a real system the simulation is modeled after. The results of the simulation may be outputted and stored in the form of data. The construction of a simulation model typically involves identifying various objects within the system, which are then represented by variables, equations or both, embodied in an "object." A simulation model may be constructed using a graphical user interface (GUI) in which the various objects are represented by user-selected icons or other appropriate graphical representations, and in which the inter-relationships between the objects are represented by links. Graphical simulation modeling may allow for a complex system to be modeled in an intuitive and visually comprehensible manner.

Computer simulations may be used to study the dynamic behaviors of environments that may be difficult or dangerous to experience or implement in real life. Simulations may assist researchers with determining and/or predicting outcomes of real-world processes by simulating the scenarios and altering one or more variables in order to view the outcome as a result of the modification to the variable(s). Simulation modeling is used to model systems to perform "what-if" analyses, to optimize system performance and to identify problems within systems.

SUMMARY

A first embodiment of the present disclosure provides a computer-implemented method comprising the steps of: selecting a simulation scenario comprising a simulation environment and an assigned role to a plurality of participants of the simulation scenario; assigning an objective for each of the plurality of participants, wherein said objective includes an acceptable stress level range for each of the plurality of participants; receiving biometric data collected by one or more biometric sensors associated with each of the plurality of participants; identifying a stress level as a function of the biometric data, associated with a participant selected from the plurality of participants, wherein said stress level is outside of the acceptable stress level range; predicting a modification to one or more elements of the simulation environment that would return the stress level of the participant back within the acceptable stress level range; and applying the modification to one or more elements of the simulation environment in real-time, during commencement of the simulation.

A second embodiment of the present disclosure provides a computer program product for modifying a simulation. The computer program product includes one or more computer readable storage media having computer-readable program instructions stored on the one or more computer readable storage media, said program instructions executes a computer-implemented method comprising the steps of: selecting a simulation scenario comprising a simulation environment and an assigned role to a plurality of participants of the simulation scenario; assigning an objective for each of the plurality of participants, wherein said objective includes an acceptable stress level range calibrated to each of the plurality of participants; receiving biometric data collected by one or more biometric sensors associated with each of the plurality of participants; identifying a stress level as a function of the biometric data, associated with a participant selected from the plurality of participants, wherein said stress level is outside of the acceptable stress level range; predicting, by the processor, a modification to one or more elements of the simulation environment that would alter the stress level of the participant back within the acceptable stress level range; and applying the modification to one or more elements of the simulation environment in real-time, during commencement of the simulation.

A third embodiment of the present disclosure provides a computer system comprising a processor; at least one biometric sensor coupled to the processor, the at least one biometric sensor receiving biometric data from a simulation participant; a computer-readable storage media coupled to a processor, wherein the computer readable storage media contains program instructions executing a computer-implemented method comprising the steps of: selecting a simulation scenario comprising a simulation environment and a role assigned to the simulation participant; assigning an objective for the simulation participant, wherein said objective includes an acceptable stress level range calibrated to the simulation participant; receiving the biometric data collected by the biometric sensor; identifying a stress level as a function of the biometric data, wherein said stress level is outside of the acceptable stress level range; predicting a modification to one or more elements of the simulation environment that would alter the stress level of the simulation participant back within the acceptable stress level range; and applying the modification to one or more elements of the simulation environment in real-time, during commencement of the simulation.

DETAILED DESCRIPTION

Overview

Figure 1:
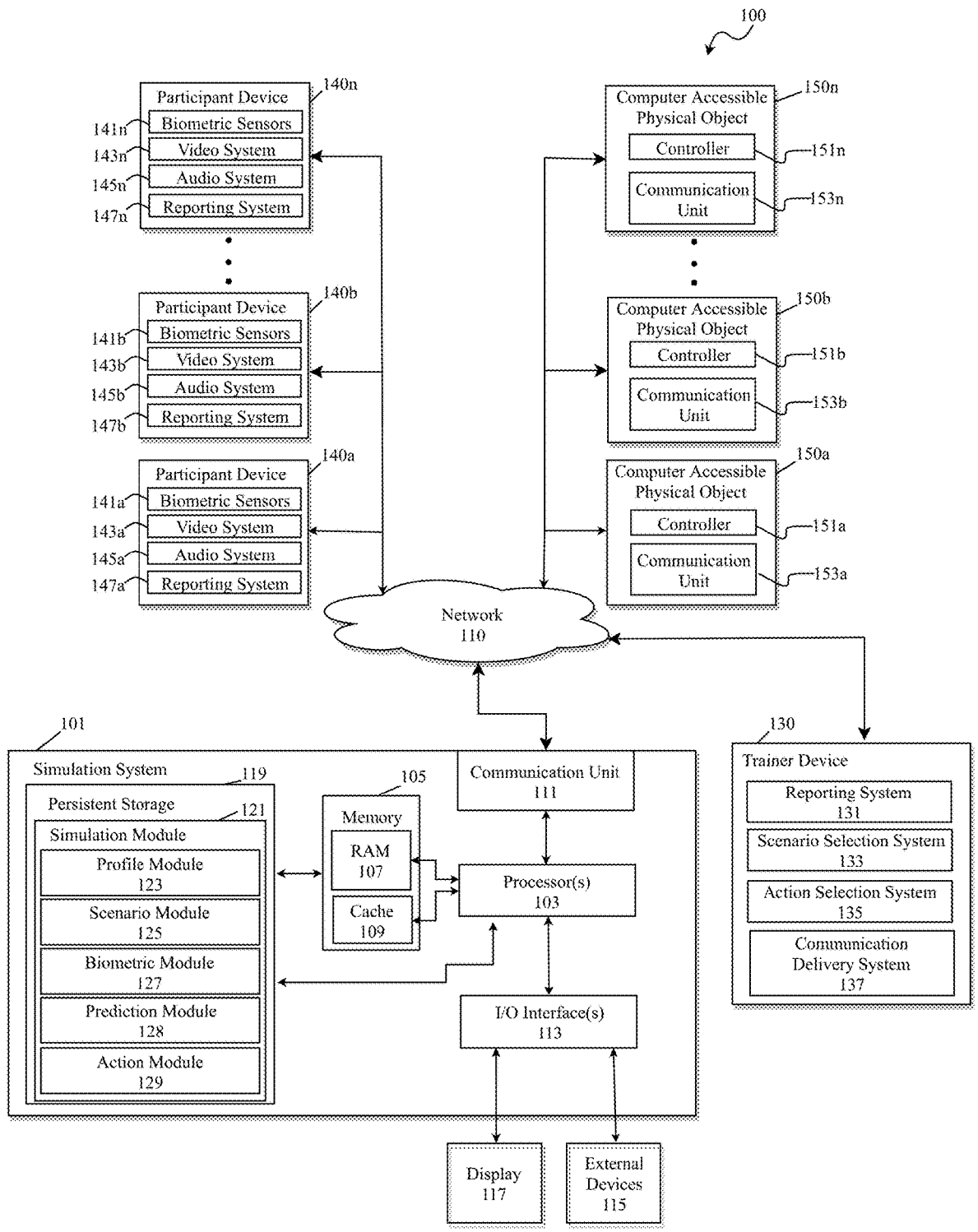
FIG. 1 depicts a functional block diagram illustrating an embodiment of a computing environment, in accordance with the present disclosure.

Training personnel may use simulations to prepare many different types of professionals for difficult and/or dangerous scenarios which may not always be predictable or safe to fully recreate. During simulated training exercises, certain conditions may be desirable for training personnel (hereinafter "trainer") to impose on simulation participants during the training simulations to maintain a desired level of stress. A trainer may desire for training simulations to be quickly adaptable and highly customizable in order to adjust simulation environments in a manner that achieves a particular objective. For example, pushing simulation participants out of the participant's comfort zone by increasing the participants stress level during the simulation. In other simulated scenarios a trainer may adjust the simulation environment to be less stressful in order to ensure participants are properly practicing skills and maintaining proper technique.

Embodiments of the present disclosure recognize that currently available training simulations rely heavily on a trainer's ability to visually recognize the simulation participants' stress levels and reactions to the changes in the simulation environment. In order to make adjustments, the trainer must manually modify the simulation environment in accordance with the trainer's objectives for each participant of a simulation scenario. Unfortunately, human capability to evaluate each simulation participant and adjust the simulation environment in real-time (or near real-time) quickly exceeds the capabilities of the trainer as the scale of the simulated scenario increases or the skill levels between simulation participants widens. It may not be practical for a human trainer to monitor the stress levels and perform the decision-making ability of multiple simulation participants simultaneously, nor may it not be practical for a human trainer to adjust the simulated scenario for one participant while simultaneously maintaining a desired level of stress or difficulty level for the plurality of remaining simulation participants.

Embodiments of the present disclosure solve the challenges associated human modification to simulations through the use of human observation and manual input, by incorporating the use of biometric data collection and computer-based predictive modeling techniques such as machine learning and Stochastic simulation. Biometric data and predictive models may reliably identify stress levels in participants and predictively adapt the simulation environment in order to manage each participants' stress levels within a desired range.

In some embodiments of the present disclosure, the systems, methods and computer program products described herein may incorporate the use of wearable devices (described below as a participant device 140a, 140b, 140n) to monitor stress levels of simulation participants. Each participant device may be equipped with biometric monitoring hardware and software, including but not limited to sensor, camera systems, microphones or other hardware and/or software. During the execution of the simulation, each wearable device may collect a participants' biometric data and stream or transmit the biometric data to a centralized simulation system 101 or a trainer's computing device 130 for further analysis and action. Embodiments of the present disclosure may analyze the collected biometric data and calculate a particular simulation participant's stress level under the current simulation environment. The participant's stress level, as determined by the participant's biometric data, may be compared to a predetermined acceptable stress level range. Stress levels falling outside of the acceptable stress level range may result in one or more modifications to the simulation environment. In some embodiments, determining the types of modifications to apply to the simulation environment and the cascading effect the modifications may have on the stress levels of all participants may be predicted using one or more predictive modeling techniques such as machine learning and/or stochastic simulation.

Embodiments of the present disclosure may select one or more modifications to the simulation environment that may be predicted to return a participant's stress level back within the acceptable stress level range, while mitigating the predicted fluctuations in stress levels of other simulation participants. Embodiments of the present disclosure may implement modifications to the simulation environment in a plurality of different manners. Modifications may alter one or more adjustable properties of a real physical object or a virtual object incorporated into the simulation environment. A "real physical object" may refer to material or matter present in physical space that may be perceived by one of the five senses, whereas a "virtual object" may refer to a computer-generated representation of a real physical object.

Embodiments of the present disclosure may be utilized in different types of simulations. For example, one type of simulation may be performed in the real-world using live participants present in a physical location. Live participants may interact with other participants, machinery, tools, devices and locales. Embodiments of the present disclosure may alter the properties of real-world objects by connecting the real-world objects to a computer network and remotely controlling the real-world objects during the simulation. For instance, modifications to real physical objects can include controlling a power supply to light sources, enabling or disabling vehicles, equipment or communication devices, locking or unlocking doors, and/or granting access to the functionality of any other object or device within the simulation environment that may be connected to a computer network.

In other types of simulations, the simulation may be performed entirely in virtual space. Participants may access the simulation environment using a computing device, similar to a playing a video game and experience the simulation by viewing the simulation using a display 117. Modifications to an entirely virtualized simulation may alter the simulation environment by changing the properties or functionality of virtual objects during the simulation. In yet other alternative embodiments, simulations may be a hybrid of both participation in the physical space of the real world as well as participating in virtual space simultaneously.

System for Modifying a Simulation

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Referring to the drawings, FIG. 1 depicts a functional block diagram of a computing environment 100, capable of modifying a simulation in accordance with the embodiments of the present disclosure. Computing environment 100 may include a simulation system 101, a trainer device 130, a plurality of participant devices 140a, 140b . . . 140n (hereinafter referenced collectively as "participant devices 140") and a plurality of computer accessible physical objects 150a, 150b . . . 150n (hereinafter referenced collectively as "physical objects 150"), interconnected via a computer network 110. As shown in FIG. 1, the number of participant devices 140 and physical objects 150 may not be limited to the number of participant devices 140 or physical objects 150 depicted in the drawings. The number of participant devices 140 and physical objects 150 may be any amount supported by network 110, wherein participant device 140n and physical object 150n identifies the last participant device 140 and physical object 150 in a plurality participant devices 140 or physical objects 150 connected to network 110 thereof and not necessarily the third participant device 140 or third physical object 150.

Figure 9A:
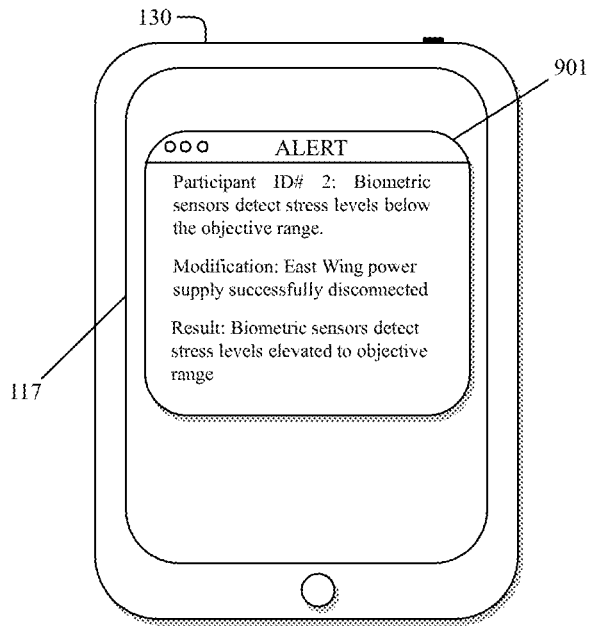
FIG. 9a depicts an embodiment of a computing device interacting with a simulation operating in an automatic simulation mode.
Figure 9B:
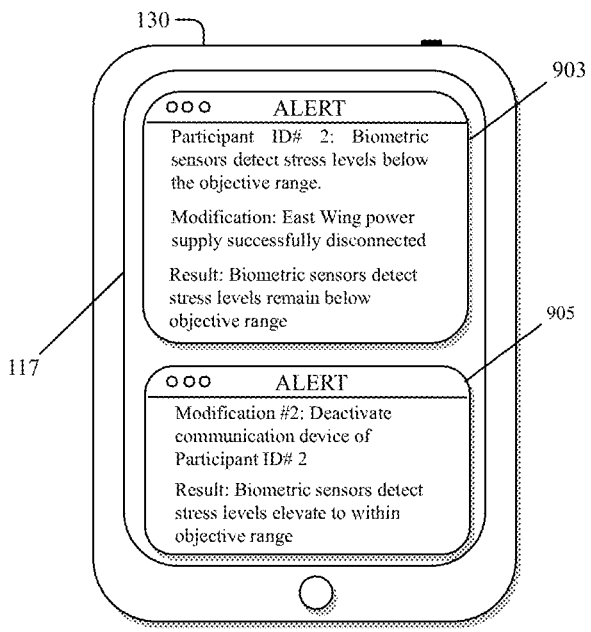
FIG. 9b depicts an alternative embodiment of a computing device interacting with a simulation operating in an automatic simulation mode.
Figure 10:
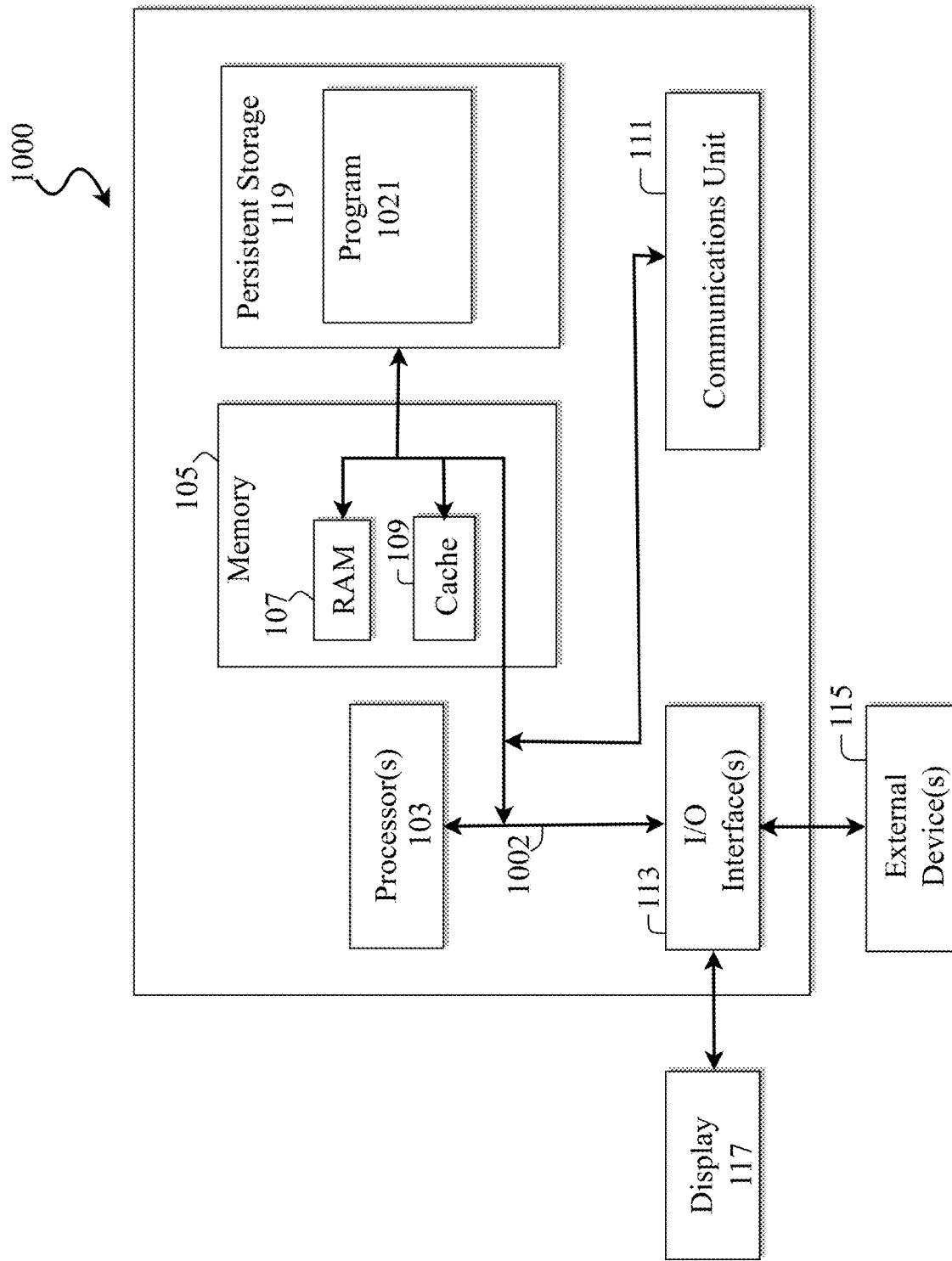
FIG. 10 depicts an embodiment of a block diagram of internal and external components of the computer systems of FIGS. 1, 7a to 9b in accordance with the embodiments of the present disclosure.

Simulation system 101, trainer device 130, participant devices 140 and physical objects 150 may each be a specialized computer system comprising specialized configurations of hardware, software or a combination thereof as depicted in FIGS. 1-3, 7-9 of the present disclosure and in embodiments described herein. Embodiments of the simulation system 101, trainer device 130, participant devices 140 and physical objects 150 may not only comprise the elements of the systems and devices depicted in FIGS. 1-3, 7-9 but may also incorporate one or more elements of a computer system 1000 as shown in FIG. 10 and described in the COMPUTER SYSTEM section detailed below. One or more elements of the computer system 1000 may be integrated into the specialized computer systems of computing environment 100, including the simulation system 101, trainer device 130, participant devices 140 and physical objects 150.

Embodiments of the simulation system 101, trainer device 130, participant devices 140 may be desktop computers, laptop computers, tablet computers, smartphones, server computers, or any other computer system known in the art. A computer accessible physical object 150 may be any device, machine or manufacture that may be capable of being connected to a computer network 110 and/or interfacing with one or more computer systems of the computing environment 100, including the simulation system 101, trainer device 130 and/or participant device 140. In some embodiments, simulation system 101, trainer device 130, participant devices 140 and physical objects 150 may represent computer systems utilizing clustered computers and components to act as a single pool of seamless resources when accessed through network 110. For example, such embodiments may be used in data center, cloud computing, storage area network (SAN), and network attached storage (NAS) applications. In certain embodiments, simulation system 101, trainer device 130, and participant devices 140 may represent virtual machines. In general, simulation system 101, trainer device 130, participant devices 140 and/or physical objects 150 may be representative of any electronic devices, or combination of electronic devices, capable of executing machine-readable program instructions, as described in greater detail with regard to FIGS. 4-6.

Embodiments of the simulation system 101, trainer device 130, participant devices 140 and physical objects 150 may each be connected and placed into communication with one another over a computer network 110. Embodiments of the computer network 110 may be constructed using wired, wireless or fiber optic connections. As shown in the exemplary embodiments, the simulation system 101, trainer device 130, participant devices 140 and physical objects 150 may connect and communicate over the network 110 using a communication unit 111 such as a network interface controller or other network communication hardware. Embodiments of the communication unit 111 may implement specialized electronic circuitry allowing for communication using a specific physical layer and a data link layer standard. For example, Ethernet, Fiber channel, Wi-Fi or Token Ring. Communication unit 111 may further allow for a full network protocol stack, enabling communication over network 110 to the group of computer systems or other computing hardware devices linked together through communication channels. The network 110 may facilitate communication and resource sharing among simulation system 101, trainer device 130, participant devices 140 and physical objects 150 and additional hardware devices connected to the network 110, for example a network accessible storage media. Examples of network 110 may include a local area network (LAN), home area network (HAN), wide area network (WAN), back bone networks (BBN), peer to peer networks (P2P), campus networks, enterprise networks, the Internet, cloud computing networks and any other network known by a person skilled in the art.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 2:
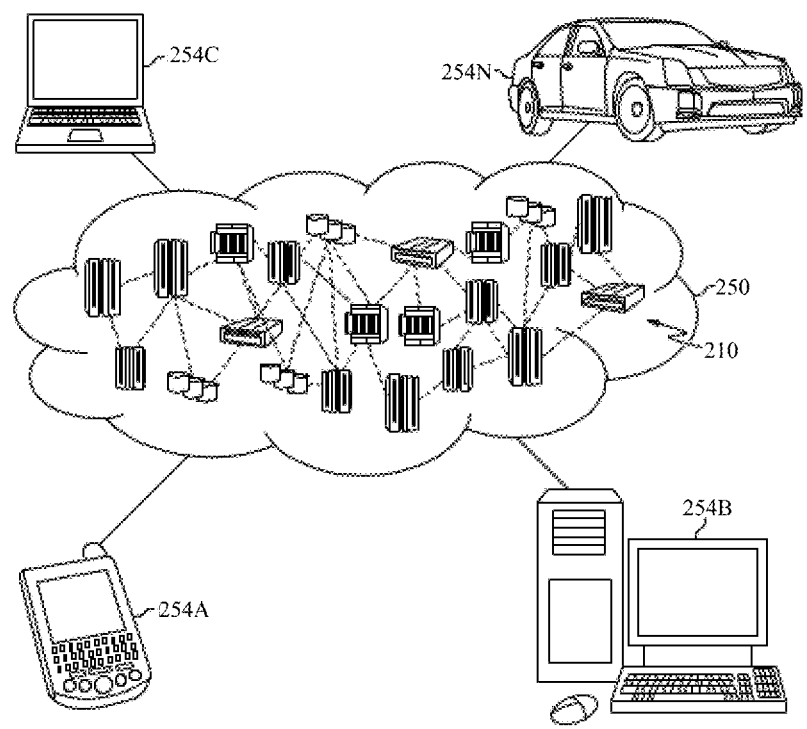
FIG. 2 depicts an embodiment of a cloud computing environment, in accordance with the present disclosure.

Referring to FIG. 2, FIG. 2 is an illustrative example of a cloud computing environment 250. As shown, cloud computing environment 250 includes one or more cloud computing nodes 210 with which local computing devices used by cloud consumers, such as, for example, smartphone or cellular telephone 254A, desktop computer 254B, laptop computer 254C, and/or any other computer network accessible physical object 150 such as an automobile computer system 254N may communicate. Nodes 210 may communicate with one another and may be grouped (not shown) physically or virtually, in one or more networks, such as Private, Community, Public, or Hybrid clouds as described hereinabove, or a combination thereof. This allows cloud computing environment 250 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
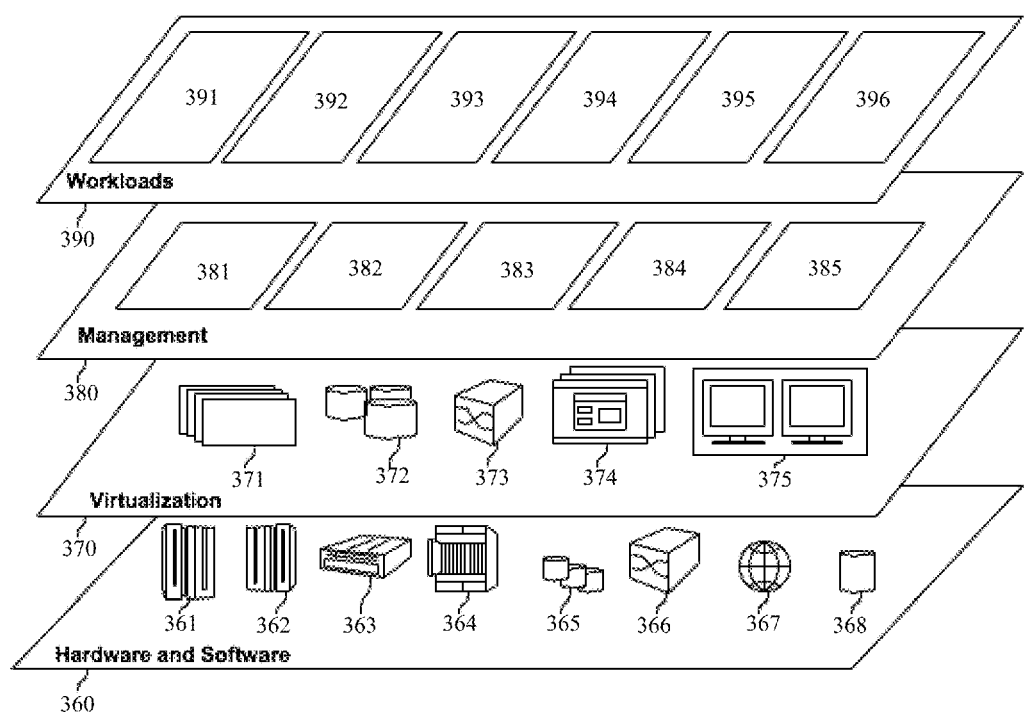
FIG. 3 depicts an embodiment of abstraction model layers of a cloud computing environment, in accordance with the present disclosure.

Referring now to FIG. 3, a set of functional abstraction layers provided by cloud computing environment 250 (FIG. 2) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture-based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395 and remote simulation processing 396 capable of running one or more of the modules 123, 125, 127, 129 of the simulation module 121, the biometric sensors 141, video system 143, audio system 145 and/or the reporting system 147 of the participant device 140 and/or the reporting system 131, scenario selection system 133, action selection system 135 and/or communication delivery system 137 of the trainer device 130 as described in detail below.

Embodiments of the simulation system 101 may include a simulation module 121. The term "module" may refer to a hardware module, software module, or a module may be a combination of hardware and software resources. A module (whether hardware, software or a combination thereof) may be designed to implement or execute one or more specific tasks, routines or functions. Embodiments of hardware-based modules may include self-contained components such as chipsets, specialized circuitry, one or more memory 105 devices and/or persistent storage 119. A software-based module may be part of a program, program code or linked to program code containing specific programmed instructions loaded into a memory 105 device or persistent storage 119 of a computer system operating in computing environment 100.

Embodiments of the simulation module 121, whether hardware, software, or a combination thereof, may perform the functions and tasks associated with selecting a simulation scenario, identifying simulation participants, setting objectives for each simulation participant, assigning roles to each simulation participant and calibrating an acceptable stress level range for each simulation participant. The simulation module 121 may further collect and monitor the biometric data of each simulation participant during the execution of the simulation, identify stress levels of each participant that may deviate from the participant's acceptable stress level range for the selected simulation scenario as a function of the biometric data collected, predict the effects of modifying the simulation environment to correct for the stress level deviation and implement one or more modifications to the simulation environment.

In the exemplary embodiment of computing environment 100 depicted in FIG. 1, the simulation module 121 may be part of simulation system 101. In alternative embodiments of the computing environment 100, the simulation module 121 may be integrated into one or more computer systems of the computing environment 100, such as the trainer device 130, participant device 140 and/or computer accessible physical objects 150. Embodiments of the simulation module 121 may comprise a series of sub-modules which may perform one or more of the specific functions or tasks of the simulation module 121. In some embodiments, the sub-modules of the simulation module 121 may comprise a profile module 123, scenario module 125, biometric module 127, prediction module 128 and/or an action module 129.

Embodiments of the profile module 123 may perform the task or function of creating, saving, storing and updating personalized information of each simulation participant. Profiles created by the profile module 123 may maintain a record of each simulation participant, including each participant's name, image of the participant, identifying information, history of past simulations the participant has participated in, a record of the participant's previously collected biometric data, stress level data, as well as any inferences, conclusions or predictions about the participant's behavior, as determined previously by the prediction module 128 (referred herein collectively as "performance data"). Each participant's profile being maintained by the profile module 123 may be continuously updated, customized and improved using the results of each subsequent simulation a participant engages in and the behaviors exhibited by the participant during each subsequent simulation.

The profile information and performance data stored by the profile module 123 may be used as a baseline or starting point for the simulation system 101 to assess and predict the behaviors, stress level impact and cognitive responses of each simulation participant while performing under various stress levels during a simulation. As the profile module 123 continues to collect and store performance data about each participant through successive simulations, the performance data may assist the predictions module 128 by streaming an increasing amount of performance data for each participant, thus allowing for more accurate prediction models to be created by the predictions module 128 using machine learning and/or stochastic simulation.

In some instances, a simulation participant may have never previously participated in a simulation implemented by simulation system 101. A new simulation participant may be prompted to create a profile which may be stored by the profile module 123. A new simulation participant may create a new profile by supplying requested information about the participant to the simulation system 101. For example, by providing the participant's name, contact information, a picture, and any other identifying information about the user. The information provided by the participant may be stored by the profile module 123 and queried by other sub-modules of the simulation module 121 and/or loaded into the memory 105 of the simulation system 101 the next time the participant is selected to participate in a new simulation.

In some embodiments, the simulation system 101 may create and store additional information about each new simulation participant in the participant's profile prior to the execution of the participant's first simulation. A pre-simulation data collection period may be used to train the simulation system 101 to improve predictions created by machine learning or stochastic simulation prior to a participant's first actual simulation. Pre-simulation data collected by the simulation system 101 may assist the prediction module 128 later on to better understand the stress level indicators of a new participant and how a new participant may respond to specific types of stress, allowing for a more precise set of predictions.

In some embodiments, a participant undergoing the pre-simulation data collection period may be connected to one or more biometric sensors 141a, 141b . . . 141n (hereinafter referred to collectively as "biometric sensors 141"), video systems 143a, 143b . . . 143n (hereinafter referred to collectively as "video systems 143") and/or audio systems 145a, 145b . . . 145n (hereinafter referred to collectively as "audio systems 145"). The simulation system 101 may engage the biometric sensors 141, video systems 143 and audio systems 145 to collect biometric data about the new simulation participants. Embodiments of the biometric data collected may include a new participant's heart rate, pulse rate, sweat levels, facial patterns, voice patterns, gait recognition, eye gaze, attentiveness, brain wave patterns, thermography and any other type of biometric data that may be known or used in the art. The types of biometric data collected may be referred to as "biometric indicators of stress" when the level of the biometric data collected infers a heightened level of stress for the particular category of biometric data. For example, an accelerated heart rate above 100 beats per minute (BPM) may be considered a biometric indicator of stress.

During the pre-simulation data collection period, new simulation participants may have their biometric data collected under conditions of varying stress levels. For example, the new simulation participant may have biometric data collected under periods of low stress, average stress and heightened stress, which may elicit a change in the biometric data collected as the stress level increases or decreases. For instance, participants may be asked to complete various tasks, puzzles or problem-solving activities with varying degrees of difficulty and stress applied. Moreover, the difficulty and stress of completing the various tasks or puzzles may be altered to be more or less stressful by implementing timing constraints. For example, the tasks may be presented under easy, average, difficult and near-impossible timing constraints. The changes exhibited in biometric data under increased or decreased stress conditions and the participant's ability to complete the requested tasks under stress may be stored by the profile module 123. The effects of stress on the new participants, the new participants ability to complete the assigned tasks and the biometric data collected as a result may be analyzed by the biometric module 127 or prediction module 128. In some embodiments, the biometric module 127 and/or prediction module may use the pre-simulation data during an actual simulation to identify elevated or decreased stress levels being exhibited by the participant. The biometric module 127 may match biometric data readings collected during an actual simulation with the biometric data previously recorded during a pre-simulation data collection period. If the biometric data matches a heightened stress level or decreased stress level, the participants' stress level may be subsequently tagged or identified as such.

The pre-simulation data collection period may also be useful for the biometrics module 127 to identify actual changes in the stress level of participants as opposed to false positives attributed to a participant's variation in physiology that may be unattributed to changes in stress levels. For example, a participant might naturally have a higher heart rate or pulse rate, higher average body temperature, prone to facial flushing, prone to excessively sweating or have a naturally nervous sounding vocal pattern when speaking publicly. Collecting pre-simulation data may allow for the simulation system 101 to compensate for the variations in the physiology of specific simulation participants. The simulation system 101 may later recognize during an actual simulation that one or more visible signs of stress in an average person may not be a sign of actual stress for specific participant. As opposed to simply attributing abnormal physiological behavior to heightened levels of stress, the simulation system 101 may compensate for the abnormal physiology in a customized manner based on the simulation system's 101 knowledge of the specific participants pre-simulation data collection period, past performance data, biometric data and stress level signs.

In some embodiments of the simulation system 101, the pre-simulation data collection period may further administer a questionnaire. Questionnaires may be conducted to gauge and predict how a particular participant may respond to one or more different situations or scenarios that may be presented within a simulation. The profile module 123 may store responses to the questionnaire within each participants' profile. The questions may include a series of fact patterns or hypothetical situations that may or may not correspond to potential situations the participant may be faced with during a simulation scenario or in a participant's day to day life. The potential situations may range from non-stressful or relaxing scenarios to moderately stressful and highly stressful scenarios. Responses to the questionnaire may be stored by the profile module 123 and analyzed by the prediction module 128. One or more conclusions about the personality, stress level responses and performance under stress may be drawn by the predictions module 128 based on each participant's response to the questionnaire.

Referring still to the drawings of FIG. 1, embodiments of the simulation module 121 may further include a scenario module 125. The scenario module 125 may be responsible for performing the task or function of storing, maintaining, transmitting and executing program data associated with one or more simulation scenarios that may be performed under the computing environment 100. Embodiments of the scenario module 125 may administer the storyline or initiate the script of a selected simulation and assign one or more roles to one or more participants engaging in the simulation. In some embodiments, the scenario module 125 may be a software platform responsible for loading and delivering the content and information comprising the simulation scenario to each participant and trainer. For example, the scenario module 125 may deliver or stream the virtual environment of a selected simulation scenario to each participant device 140 and/or trainer device 130. Simulation scenarios loaded and administered by the scenario module 125 may, in some embodiments be selected by personnel administering the simulation such as a trainer, specifically selected by the simulation system 101, randomly selected by the simulation system 101 and/or selected or voted on by one or more participants.

In some embodiments of the simulation system 101, the scenario module 125 may be tasked with managing a database, repository or other type of data structure comprising information, properties and variables describing each virtual object and/or real physical objects 150 that may be present in a selected scenario's simulation environment. The fields of the database may include fields comprising one or more modifiable properties of the virtual objects and real physical objects 150. As the participants interact with the simulation or the simulation is modified, the fields describing the physical objects 150 and/or virtual objects of the simulation environment may be altered or modified by the scenario module 125. The scenario module may update the simulation environment to properly reflect the current state of the simulation's objects (both physical objects 150 and/or virtual objects) as modified during the commencement of the simulation.

In some embodiments of the simulation system 101, the scenario module 125 may further perform the task or function of tracking and reassigning roles to participants of the simulation as the simulation progresses. During a live action simulation, certain participants may be assigned roles or a script to follow. For example, in a natural disaster rescue simulation to train first responders, a participant may be assigned the role of a patient or rescue who has a particular status or condition. At some point during the simulation, the status or condition of the patient or rescue may change. For instance, the participants condition may change from stable to critical as a way to test other participants tasked with saving the participant during the natural disaster rescue simulation. The scenario module 125 can assign, track, and update the roles and status changes associated with the roles as the roles change in real time or near real time throughout the simulation. Using the example of the patient condition above, embodiments of the scenario module 125 may be responsible for assigning a change in the role of the simulation participant from a patient in stable condition to a patient in critical condition or severely critical condition. The scenario module 125 can then update a database, log or other data structure to accurately reflect the role change. The participant may be alerted of the change in role and the participant may proceed to alter the participant's behavior accordingly to accurately simulate a patient who has experienced a dramatic change in their condition, had occurred in real life.

Embodiments of the simulation module 121 may further comprise a biometric module 127. The biometric module 127 may be responsible for performing functions and tasks associated with sending, receiving, analyzing and storing biometric data collected from one or more participants and/or participant devices 140 associated with each of the simulation participants. The biometric module 127 may be tasked with analyzing biometric data for signs of stress level and assigning a stress level to the participant as a function of the biometric data collected and analyzed. Embodiments of the biometric module 127 may interface with each participant device 140 over network 110. Each participant device 140 may be equipped with biometric collecting hardware and/or software. Participant devices 140 may include any type of portable computing devices such as smart phones, laptops, tablets, personal data assistants (PDA), and portable media players. Participant devices 140 may be wearable computer devices such as wrist bands, watches, badges, ID cards or any other device capable of being equipped with one or more biometric system.

FIG. 1 of the drawings depicts a plurality of participant devices 140 that may collect and stream biometric data over network 110 to the biometric module 127. Biometric systems equipped on the one or more participant devices 140 may include biometric sensors 141, video system 143a, 143b . . . 143n (hereinafter "video system 143") and/or audio system 145a, 145b . . . 145n (hereinafter "audio system 145"), which may separately or in combination of one another collect biometric data of participants. The term "biometric" may be described as the measurement and analysis of unique physical or behavioral traits and may be unique to a participant's personal identity. Embodiments of biometric sensors 141 may be described as a transducer that changes the biometric measurement of a person (in this case participants wearing the participant device 140) into an electrical signal. Embodiments of biometric sensors 141 may read or measure different types of energies such as light, temperature, speed and/or electrical capacity. Biometric sensors 141 may be optical sensors, CCD or CMOS image sensors, solid state sensors which may operate using thermal, capacitive, or piezoelectric sensors, electric field sensors, ultrasound sensors and/or any other type of sensor known or used in the field of biometrics.

As shown in FIG. 1 each of the biometric sensors 141 may be coupled with a video system 143 and/or an audio system 145. Embodiments of the video system 143 may include a high definition and/or biometric camera(s), while audio system 145 may include one or more microphones for capturing sound and/or voice data. Using a combination of biometric sensors 141, video system 143 and/or audio system 145, each participant device 140 may collect biometric data from participants throughout the entire course of the simulation. Biometric data collected by the participant device 140 may be transmitted to the biometric module 127 where the biometric data may be analyzed for signs of stress and a current stress level for each participant associated with the biometric data may be calculated. Current stress levels identified as a function of the biometric data may be compared with stress level ranges set for each participant by the simulation system 101 or trainer. Examples of biometric data that may be collected by the participant device 140 may include each participant's heart rate, pulse rate, blood pressure, sweat level, voice pattern (and changes in voice pattern), attentiveness level, eye gaze, gait, facial expressions and/or body temperature.

Moreover, in some embodiments, biometric data may also be used to identify each participant while the participant is operating in the simulation environment. For example, biometric sensors 141, video system 143 and/or audio system 145 may use physiological or behavioral biometrics to identify participants using facial recognition, fingerprint, palm print, hand geometry, iris recognition, ear recognition, tooth-shape, retina recognition, DNA, voice pattern recognition, keystroke, signature and any other biometric measurement that may be known or used. In some alternative embodiments, each participant in a simulation may not wear a participant device 140. Instead, a simulation environment may be outfitted with one or more biometric systems to create a "smart environment" that identifies each participant as well as watch and record participant behavior and ascertain biometric data without being specifically worn by the participant themselves.

In some embodiments of the simulation module 121, a prediction module 128 may be included as shown in the drawing of FIG. 1. Embodiments of the prediction module 128 may perform the task or function of predicting the effects of modifying a simulation environment on the stress levels of each simulation participant. The prediction module 128 may analyze and predict the results of altering one or more properties of physical objects 150 and/or one or more virtual objects of the simulation environment and determine whether or not such alterations to the simulation environment will re-establish a participant's stress level back within an acceptable stress level range. Not only are predictions of the directly affected simulation participant's stress level taken into consideration, the predictions module 128 also uses machine learning or stochastic simulation to forwardly predict one or more effects altering the simulation environment on the stress levels of additional simulation participants who may be either directly or indirectly affected. In some embodiments, prediction module 128 may also consider the effects of altering one or more roles assigned to simulation participants and predict the effects of a role change on each of the stress levels of each simulation participants.

Embodiments of the prediction module 128 may utilize machine learning techniques to model and predict the anticipated responses a simulation participant may exhibit in the participant's stress level and biometric data while experiencing one or more modifications to the simulation environment. "Machine learning" may refer to computer system techniques and algorithms that enable a computer system to learn over time in an autonomous fashion by feeding data and information to the computer system in the form of observations and real-world interactions. In computing environment 100, the prediction module 128 may use a combination of biometric data collected by the biometric module 127, stress levels calculated as a function of the biometric data and observable behaviors (i.e. observations recorded using one or more video systems 143 or audio systems 145) of participants operating at a particular specific stress level to recognize patterns in each simulation participant's behavior. The prediction module 128 may parse the changes in biometric data and participant's observed response to a situation occurring at a particular stress level in order to predict how future changes to the simulation environment will subsequently affect each participant. More specifically, the predictions module 128 may be tasked with correcting for stress level deviations outside of an acceptable stress level range and implementing modifications to the simulation environment that will be predicted to return a participant's stress level back within the acceptable stress level range. Returning the participant to the acceptable stress level range may include modifying the simulation environment to increase or decrease stress on the participant as observed through the collection of biometric data.

Embodiments of a machine learning algorithm incorporated into a predictions module 128 may be developed using one or more learning styles such as supervised learning, unsupervised learning or a combination of learning styles thereof. The predictions module 128 may apply the learning technique to a specific type of modeling technique in order to predict the effects of modifying the simulation environment on the stress levels of one or more simulation participants. Examples of machine learning modeling techniques may include, but are not limited to classification, regression, decision tree modeling, Gaussian mixture models, clustering, deep learning, or any other machine learning modeling technique known by a person skilled in the art.

"Supervised learning" may refer to training the prediction module 128 using a data set containing training examples that may already have known correct answers in order to teach the predictions module 128 to identify patterns in how participants will respond to one or more changes in the simulation environment. When using supervised learning methods, examples of the correct inputs may be used to show the prediction module 128 of the simulation system 101 the correct input-output pairs, which may be performed during a training phase. Supervised learning may allow the prediction module 128 to find a correct answer for how to modify a simulation environment for one or more participants, based on previous examples of correct answers to choose from or draw inferences. Supervised learning may occur during the pre-simulation data collection period in some embodiments. In alternative embodiments, the prediction module 128 may learn from past participant behavior in previous simulations that are subsequently analyzed and used as a training examples to teach the predictions module 128 how to better predict the behavior of simulation participants.

In embodiments utilizing supervised learning, the prediction module 128 may attempt to learn the relationship between modification of the simulation environment and stress level by running previously labeled training data (i.e. data that has been classified or categorized) through a learning algorithm in order understand the way specific participants may respond to various changes in their environment. Based on the labelled training data, the predictions module 128 may learn whether certain simulation environment modifications to physical objects 150, virtual objects or the assigned roles of participants during a simulation will be expected to result in an increase, decrease or have no effect on the participant's stress levels as a result of the modification.

"Unsupervised learning" on the other hand may allow for the prediction module 128 to find patterns in the biometric data, stress levels and participant specific responses to the modifications of the simulation environment, without undergoing a specific training period as used in supervised learning. In some embodiments of the predictions module 128 that use unsupervised learning, the predictions module 128 may use clustering to group observations of similar or common groups of simulation participants who may respond to stress altering variations of the simulation environment. Based on the data of previous simulation participants that have responded in a similar observable pattern, the predictions module 128 may predict other simulation participants having the same personality or other observable responses that may also behave in a similar manner and thus make predictions according to an expected behavior of simulation participants having similar behavioral characteristics and traits.

In some embodiments of the computing environment 100, the simulation module 121 may comprise an action module 129. Embodiments of the action module 129 may be responsible for performing the task or function of implementing a modification to the simulation environment that may have been predicted by the prediction module 128 to adjust the stress level of a simulation participant back within the acceptable stress level range assigned for the particular simulation scenario being executed. Actions implemented by the action module 129 may include modifications to one or more properties of a virtual object represented a virtual space of a simulation environment, a modification to one or more properties of physical objects 150 and/or changes to one or more roles previously assigned to one or more simulation participants.

Embodiments of the action module 129 may communicate the selected modifications of virtual objects within a simulation environment by transmitting a request to the scenario module 125 requesting a change to one or more properties of the virtual objects selected for modification. Upon receiving the request for modification, the scenario module 125 may amend the properties of the selected virtual object and alter the virtual space of the simulation environment to properly reflect the change on display 117 of each participant device 140 and/or trainer device 130. For example, a simulation operating in virtual space may include a disaster relief rescue, such as an evacuation of hospital patients. As part of the simulation, virtual objects such as doors requiring keycard access may be used and/or patients that may have varying levels of stability and conditions suitable for being moved from the hospital. An objective of the simulation may be to maintain a heightened level of stress on each of the simulation participants. If the biometric module 127 has identified levels of stress that are below the acceptable stress level in simulation participants, the prediction module 128 can identify and predict modifications to increase the stress level of the simulation, such as making the virtualized hospital more difficult to traverse by locking specific virtual doors or deteriorating the conditions of various virtual patients. In accordance with the prediction module's 128 predictions, the action module 129 can implement the changes via the scenario module 125 to lock virtual doors and alter the state of virtualized patients, making the simulation more stressful and increasing participant stress levels.

In addition to modifying virtual objects, embodiments of the action module 129 may modify a live action simulation that may be occurring in real physical space. The action module 129 may implement changes to the simulation environment by changing one or more properties of one or more computer accessible physical objects 150. Embodiments of action module 129 may make changes the properties of the physical objects 150 by communicating with one or more computer accessible physical objects 150 via network 110. Embodiments of the physical objects 150 may comprise a controller 151a, 151b ... 151n (herein referred to collectively as "controller 151") and/or a communication unit 153a, 153b ... 153n (hereinafter referred to collectively as "communication unit 153"). The action module 129 may either communicate with communication unit 153 directly or indirectly via scenario module 125 by transmitting a request to change one or more properties of the physical object 150.

The request to modify one or more properties of the physical object 150 may be received by the communication unit 153 and controller 151 may implement the modification to the physical object by adjusting one or more properties of the physical object 150. For example, in a simulation of a disaster relief rescue using a real physical location such as a hospital and first responders carrying out the rescue in the real-life physical world, various portions of the hospital's simulation environment can be altered based on the objectives of the simulation system 101 for the particular scenario and the acceptable stress level ranges desired to be maintained by the first responders participating in the scenario.

Similar to the virtualized scenario described above, physical variations of real-world objects may also be modified to alter the stress levels of the first responders acting as simulation participants. For example, in the hospital setting described above, various doors may contain electronically controlled locks and lights may be electronically controlled as well. Each electronic door and lighting system may be connected to network 110 and controlled by controller 151 associated therewith. During the simulation of the disaster relief rescue, it may be desirable by the trainer or simulation system 101 to maintain a heightened level of stress within the acceptable stress level range. To increase stress levels, the prediction module 128 predicts that increasing the difficulty of the scenario by locking doors and decreasing visibility of the first responders may maintain the stress levels of the first responders within the acceptable stress level. Accordingly, the action module 129 may request one or more controllers 151 operating one or more specific electronically lockable doors be modified to the locked state. Likewise, the action module 129 may further transmit a request to one or more controllers 151 connected to one or more lighting systems within the hospital be set to an off state. Accordingly, in response to the requests of the action module 129, the locking the selected doors and turning off specific lighting systems can be performed remotely in accordance with the predictions of the prediction module 128. Subsequently, the biometric module 127 continues to sample the biometric data being received from the first responders, to confirm that the stress levels have been elevated as predicted to within the acceptable stress level range as a result of the changes to the properties of the doors and lights.

In some embodiments, the action module 129 may communicate via network 110 with participant devices 140 to describe updated or reassigned roles to simulation participants. Each participant device 140 may be equipped with a reporting system 147a, 147b ... 147n (hereinafter referred to collectively as "reporting system 147") capable of receiving and displaying notifications. In some embodiments of simulations, one or more participants may be assigned a role to act out as part of the simulation. Modifications to the simulation environment may include one or more changes to the assigned roles of simulation participants to increase or decrease the stress level of participants acting out a specific role and/or other simulation participants they may interact with. For example, in a disaster relief rescue mission, one or more participants may be patients stranded in a hospital. Each patient may have a set condition or status at the onset of the simulation that may be modified. At a certain point during the simulation, the prediction module 128 can determine that one or more participants may require an increased stress level to maintain another participants stress level within the acceptable stress level range (i.e. inflict a stressful situation on a participating first responder participating within the simulation). An action module 129 may implement a solution derived from the prediction module 128 predictions. For example, one solution for achieving the increased stress level may be by placing a patient in a new status, such as a patient undergoing cardiac arrest. The action module 129 can communicate with one or more participant devices 140 via network 110 by sending a notification of the change in role to the simulation participant acting out the role of the patient and the participant may change their demeanor from a stable status to a cardiac arrest status.

In some embodiments of the computing environment 100, one or more trainers may have varying levels of control over the actions and modifications to the simulation environment. Computing devices, which may be referred to herein as trainer devices 130 may operate in a different manner than participant devices 140. More specifically, the trainer devices 130, may, depending on the simulation system 101, exert control over the simulation scenarios being selected, the modifications being applied to the simulation environment and communications being sent between the simulation system 101, the trainer device 130 and/or the participant device 140.

Embodiments of a trainer device 130 may include a reporting system 131. The reporting system 131 may receive notifications and messages from the simulation system 101 regarding the simulation's status, participant updates, modifications to the simulation environment and/or requests for input from the simulation system 101. The reporting system 131 may display the notifications or messages to a trainer operating the training device 130 via a display 117. The level of reporting and input capabilities afforded to the trainer device 130 may depend on the mode of operation that may have been selected for the simulation environment. Operating modes may include a manual, semi-automatic or fully automatic operating mode.

Under a trainer device 130 operating in manual mode, notifications 701 received by the reporting system 131 may be sent to the training device 130 and display observations of the changes in biometric data or stress levels of the simulation participants as a function of the stress level changes. Conversely, while operating under a semi-automatic mode, notifications 801 received or displayed by the reporting system 131 may include not only notifications describing observed changes in biometric data and/or stress levels of participants but also a recommended modification to re-establish each participant's stress level within the acceptable stress level range. Moreover, a trainer device 130 operating in fully automatic mode, may receive alerts 901, 903 describing changes in biometric data and/or stress levels of participants, the modification implemented by the simulation system 101 to re-establish stress levels within the acceptable stress level range and information describing the success of the modification in re-establishing stress levels of the participant.

In some embodiments of the computing environment 100, the trainer device 130 may include a scenario selection system 133. Embodiments of the scenario selection system 133 may allow for the trainer operating the trainer device 130 to specify which simulation scenario should be loaded by the scenario module 125 of the simulation system 101. Embodiments of the scenario selection system 133 may also allow for, as part of the scenario selection process, a trainer to manually set or adjust one or more objectives for simulation participants, including configuring the acceptable stress level ranges. Manual control over the selected simulation scenario and the level of stress a trainer would like to target for one or more participants allows for the trainer to ensure that a participant is developing skills for real life scenarios being tested by the simulation. By maintaining either a low level of stress, the trainer may allow the participant(s) to develop new skills in a controlled environment, with few distractions or under elevated levels of stress which may teach the participant to complete tasks under pressure. However, in alternative embodiments, the trainer device may be notified of the pre-selected stress level ranges selected by scenario module 125 for each participant. In some embodiments, the trainer may adjust or override the acceptable stress level ranges presented.

Figure 7A:
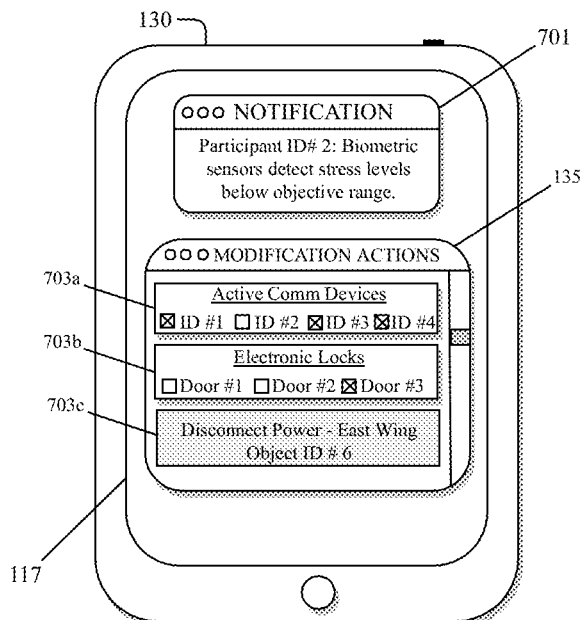
FIG. 7a depicts an embodiment of a computing device interacting with a simulation operating in a manual simulation mode.
Figure 7B:
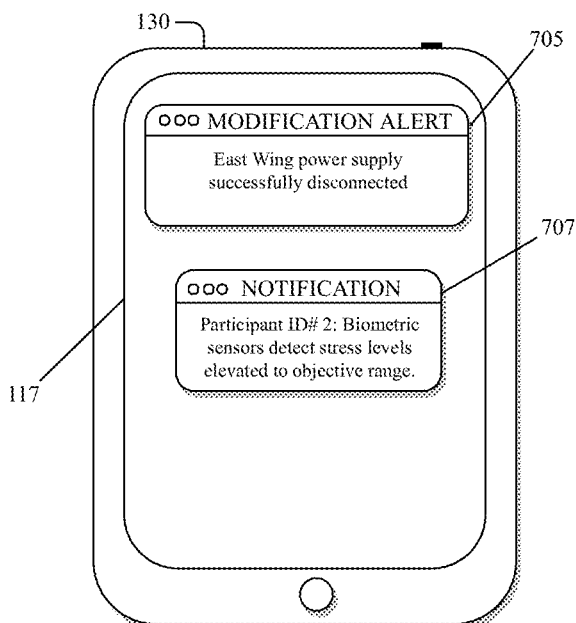
FIG. 7b depicts an embodiment of the computing device of FIG. 7a, interacting with a simulation operating in a manual simulation mode.
Figure 8A:
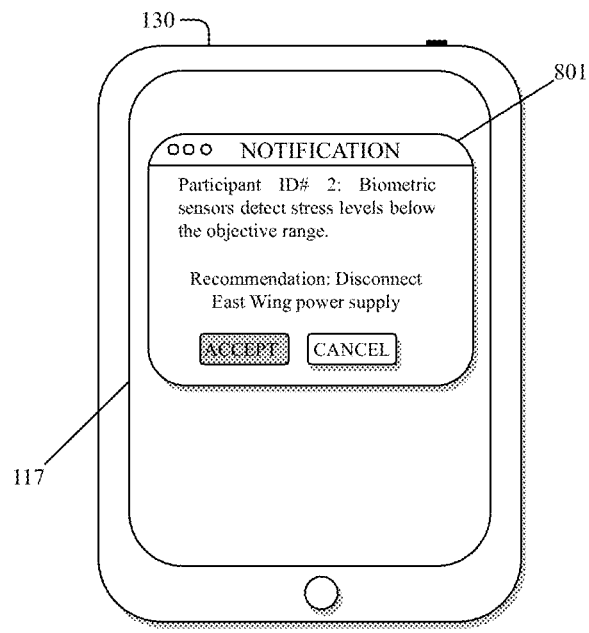
FIG. 8a depicts an embodiment of a computing device, interacting with a simulation operating in a semi-automatic simulation mode.
Figure 8B:
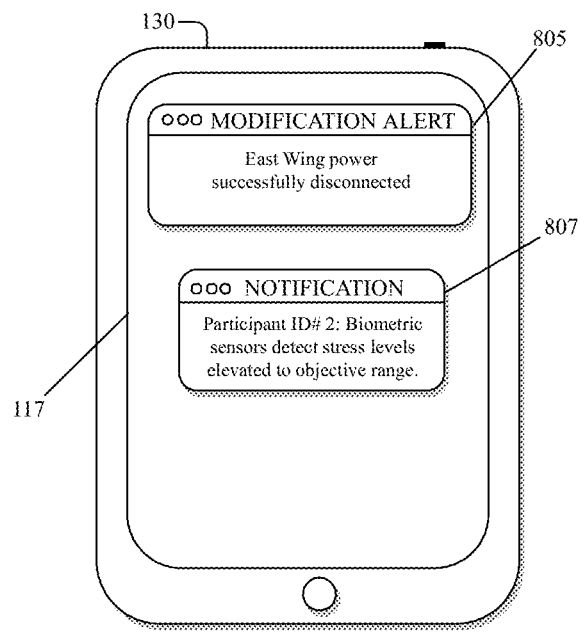
FIG. 8b depicts an embodiment of the computing device of FIG. 8a interacting with a simulation operating in a semi-automatic simulation mode.

Embodiments of the trainer device 130 may further include an action selection system 135. Embodiments of the action selection system 135 may vary depending on whether the trainer device 130 is operating in manual, semi-automatic or fully automatic modes. Embodiments of the action selection system 135 allow for the trainer device to select and/or authorize one or more modifications 703*a*, 703*b*, 703*c* to the simulation environment during the commencement of a simulation, as shown in the example of FIGS. 7*a*, 7*b*. The action selection system 135 may communicate with the action module 129 by transmitting requests via network 110 instructing the action module 129 to implement one or more modifications 703*a*, 703*b*, 703*c* to the simulation environment. While operating in manual mode, the action selection module may provide a list of one or more modifications that a trainer may select from for implementation on the simulation environment. Conversely, embodiments of the trainer device 130 operating in semi-automatic mode as shown in FIG. 8*a* may receive a suggested modification notice from the simulation system 101. The trainer may, via the action selection system 135 approve or cancel the request for implementing the proposed modification. The approval or denial of the modification request may be transmitted by the action selection system 135 via network 110 to the action module 129.

Embodiments of the trainer device 130, may further include a communication delivery system 137. Embodiments of the communication delivery system 137 may be responsible for performing the task or function of providing messaging and/or voice communication between the trainer device 130 and/or the participant devices 140. The communication deliver system 137 may allow for a trainer to communicate directly with simulation participants, allowing for guidance and directions as well as a direct human assessment of the participants stress or status. The trainer may also communicate changes in a participant's role in the simulation directly to the participant and/or stream updated dialogue or a script to the participant device 140, that the trainer would like to use during the simulation.

Method for Modifying a Simulation

Figure 4:
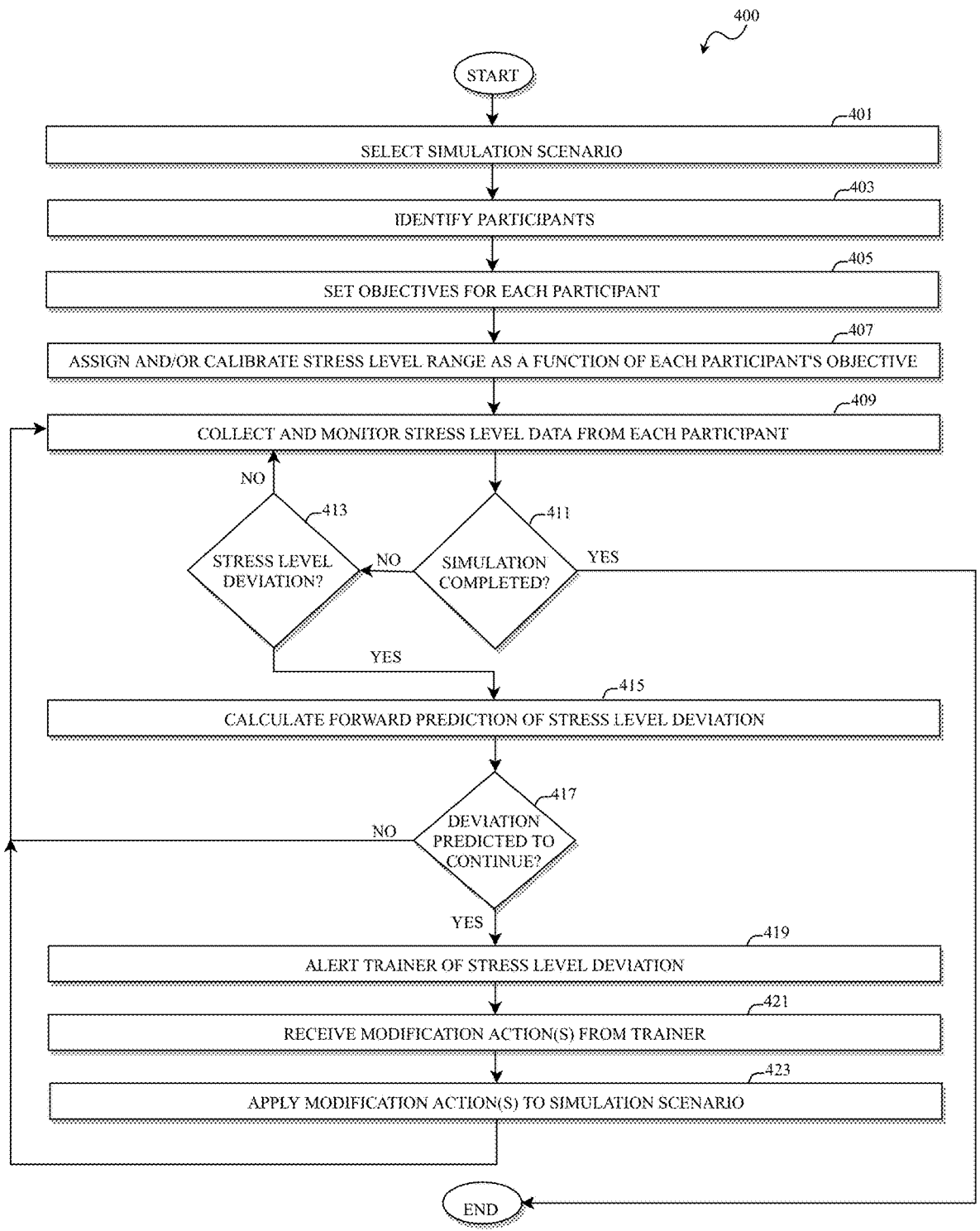
FIG. 4 depicts a flowchart illustrating an embodiment of an algorithm for modifying a simulation operating in a computing environment, in accordance with the present disclosure.
Figure 5:
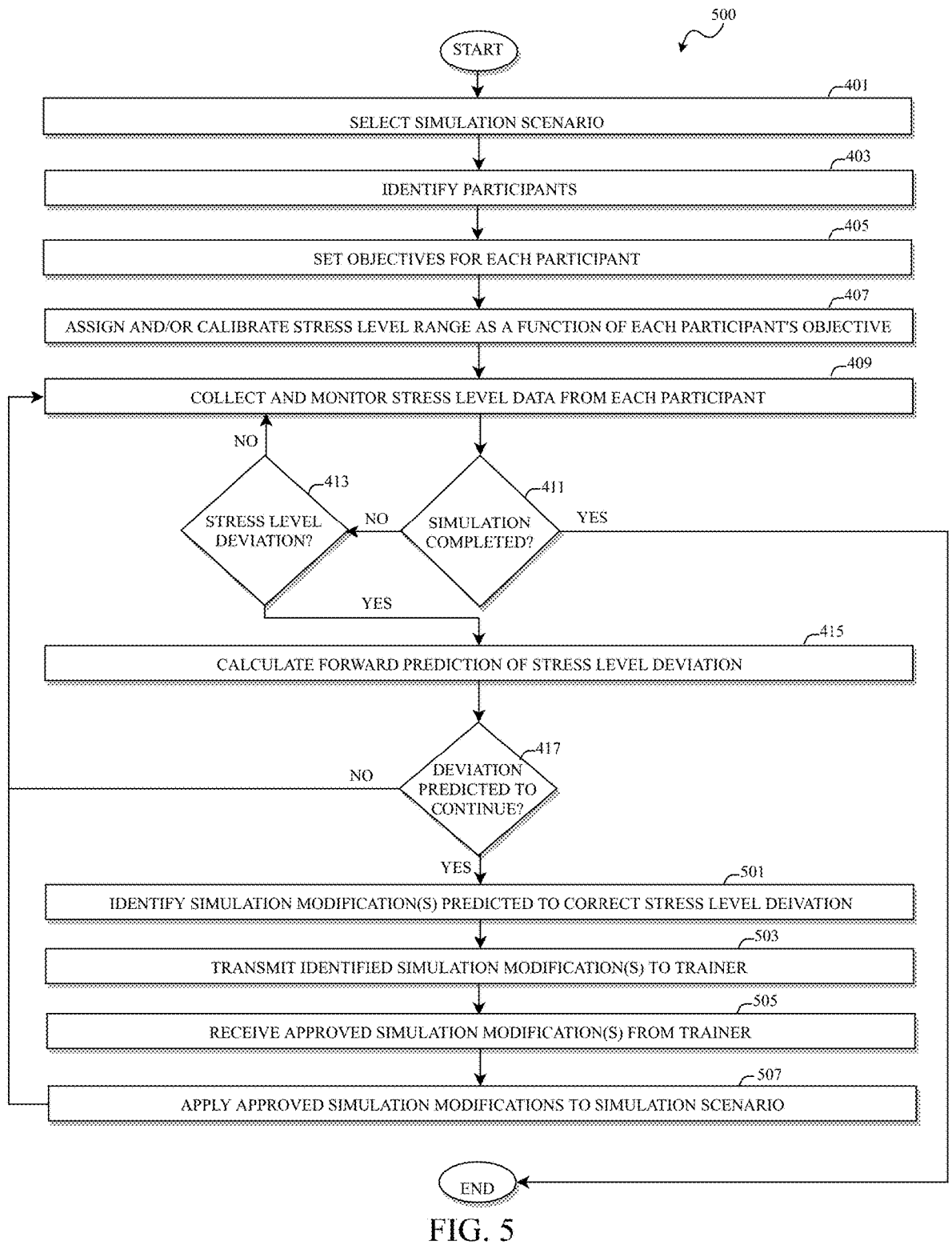
FIG. 5 depicts a flowchart illustrating an alternative embodiment of an algorithm for modifying a simulation operating in a computing environment, in accordance with the present disclosure.
Figure 6:
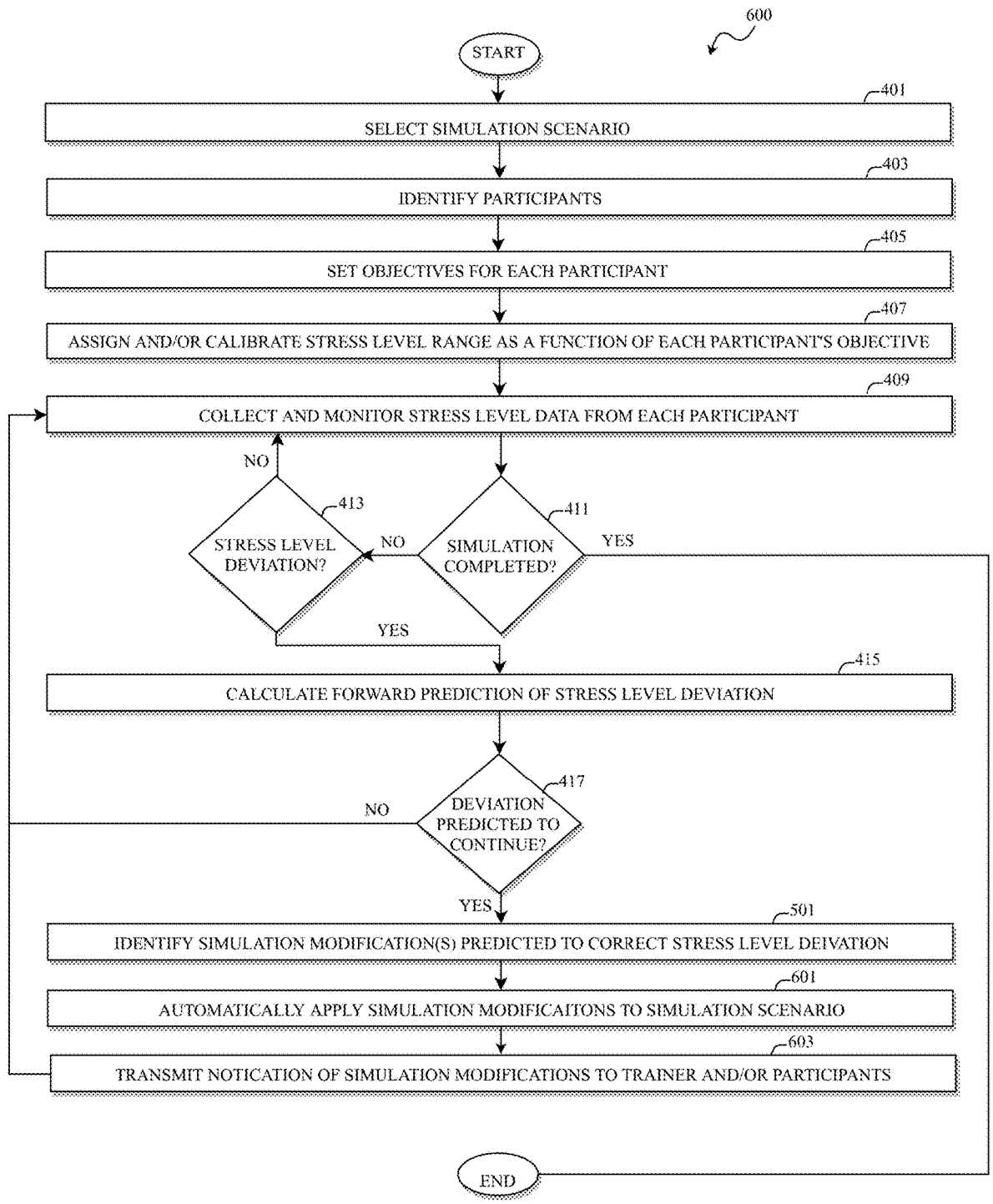
FIG. 6 depicts a flowchart illustrating another alternative embodiment of an algorithm for modifying a simulation operating in a computing environment, in accordance with the present disclosure.

The drawings of FIG. 4-6 represent embodiments of a method or algorithm that may be implemented for modifying a simulation in accordance with the computing environment 100 described in FIG. 1-3 and FIG. 7-9, using one or more computer systems as defined generically by computer system 1000 in FIG. 10 below and more specifically by the embodiments of specialized computer systems depicted in FIG. 1-3 and FIG. 7-9. A person skilled in the art should recognize that the steps of the algorithm described in FIG. 4-6 may be performed in a different order than presented and the algorithms of FIG. 4-6 may not require all the steps described herein to be performed. Rather, some embodiments may alter the algorithm by using one or more of the steps discussed below.

FIG. 4 is a flowchart illustrating an algorithm 400 for modifying a simulation, in accordance with the embodiments of the present disclosure. The embodiment of the algorithm 400 may begin at step 401. In step 401, a simulation scenario may be selected for the next simulation to be executed. In some embodiments of algorithm 400, the simulation scenario may be selected by a trainer operating a trainer device 130 via a scenario selection system 133. The trainer may view one or more possible scenarios using the trainer device 130 listed by the scenario selection system 133. Upon selecting a scenario chosen by the trainer, the scenario selection system 133 may transmit a request via network 110 to the simulation system 101 to load the selected scenario. Scenario module 125 of the simulation system 101 may queue up or load the selected scenario into the memory 105 of the simulation system 101. Upon the selection of the scenario, the algorithm 400 may continue on to step 403.

In alternative embodiments of step 401, a trainer may not select a scenario via the scenario selection system 133. Instead, in some embodiments, the scenario module 125 of the simulation system 101 may already have a pre-set or predetermined scenario that may be scheduled to be loaded. Alternatively, in other embodiments, the simulation scenario may be randomly selected by the scenario module 125 or participants and/or trainers may electronically vote for the simulation scenario to run. Votes may be electronically transmitted from the participant devices 140 and/or trainer devices 130, wherein the scenario module 125 may tally the votes and load the simulation scenario receiving the highest vote total.

In step 403 of algorithm 400, the simulation system 101 may identify each of the simulation participants that may be participating in the selected simulation scenario. Identification of participants in step 403, in some embodiments, may be performed by each participant device 140 by loading a corresponding participant's profile from profile module 123 via network 110. As each participant device connects to network 110 and loads a profile, the profile module 123 may track the participant devices 140 connected to the simulation system 101 and the corresponding profile loaded into the memory 105. New participants may connect to the simulation system 101 using a participant device 140 via network 110 and request the creation of a new profile. The profile module 123 may request identifying information about the participant, create and store the newly created profile. New participants in some embodiments may further proceed to completing a pre-simulation data collection period prior to the initiation of the selected scenario. Upon the identification of each participant (new or returning), the algorithm 400 may proceed to step 405.

In step 405 of algorithm 400, the scenario module 125 may set one or more objectives for each participant. Objectives for each participant may define the roles of each participant during the simulation, the difficulty level of the simulation scenario and/or level of stress the participant should be engaging with the scenario. For example, objectives of the participant can set based on the amount of stress a participant is expected to feel during the course of the simulation scenario. For instance, the objective amount of stress may be low, med or high. The objectives may be set by the trainer using the scenario selection system 133 in some embodiments. In alternative embodiments, the objectives may be pre-set by the scenario module 125 for each participant (with or without further input from the trainer), assigned based upon the level of experience and the number of simulations a participant has previously participated in (as recorded by the participant's profile) or randomly selected by the scenario module 125.

In step 407 of algorithm 400, embodiments of the simulation system 101 may assign and/or calibrate each participant's acceptable stress level range as a function of the objective set for each participant in step 405 of the algorithm 400. Embodiments of the acceptable stress level ranges may be assigned or managed by the biometric module 127 using historical biometric data collected from each participant in past simulations as well as pre-simulation data collection periods. The objectives set for each participant in step 405 may determine whether a participant in the simulation scenario should have their stress level maintained at a low, medium or high level during the simulation. Based on the objective set for each participant's stress level, the biometric module 127 may customize the acceptable stress level range for each participant using the past biometric data as indicators of a participant's stress level, past physiological behavior and known physiological abnormalities which may or may not be an actual sign of stress in the participant.

Each participant's acceptable stress level range may vary in size and the overall number of biometric indicators that may be considered for a participant to be within a range of low, medium or a high amount of stress. For example, one participant may have a variation in heart rate above 80-120 beats per minute (BPM) before they start to exhibit other signs of high stress levels, such as excess sweating, nervous vocal patterns, above average skin temperatures, etc. Conversely, another participant may not exhibit indications of being under a high level of stress until a heart rate is above 160 beats per minute, however the latter participant may have a higher than normal resting heart rate that may need to be compensated for when determining whether a stress level should be considered in the high, medium or low range.

In alternative embodiments, the acceptable stress level ranges may be based on the number of different biometric indicators for stress and the calculated level of stress for each biometric indicator. Each biometric indicator may be calibrated to find the resting or average level for the participant under a non-stressful scenario and scaled up based on biometric data previously collected by the biometric module 127. For example, an acceptable range for low stress may be considered 0-1 biometric indicators of stress and a heart of 60-100 BPM, whereas a medium level of stress may be a heart rate of 100-130 BPM and 2-4 biometric indicators of stress (i.e. excess sweating, shaking palms, nervous vocal pattern, facial flushing, elevated body temperature, etc.) and a high level of stress may be a heart rate in excess of 140 BPM and 5+ biometric indicators of stress.

In step 409 of the algorithm 400, embodiments of the biometric module 127 may collect and monitor the biometric data from each participant. The biometric module 127 may receive biometric data from the biometric sensors 141, video system 143 and/or audio system 145 of each participant device 140, throughout the entire simulation, until the simulation has completed. The biometric data collected from each participant device 140 may be analyzed for one or more indicators of stress in the participant. As the biometric module 127 collects and monitors the stress levels of the participants as a function of the biometric data, the algorithm may proceed to step 411 to determine whether or not the simulation has completed. If the simulation has completed, the algorithm may proceed to end and cease the collection and monitoring of biometric data. Alternatively, if the simulation has not been determined to have ended in step 411, the algorithm 400 may proceed to step 413.

In step 413 of the algorithm 400, the biometric module 127 may determine whether or not the stress level of each participant has deviated from the acceptable stress level range which may have been set based on the objective of the participant prior to the initiation of the simulation. Embodiments of the biometrics module 127 may analyze the biometric data for one or more indicators of stress in the participant. Based on the analysis of the indicators of stress, the biometric module 127 may compare the current biometric data and indicators of stress against the acceptable stress level range to identify whether or not the participant has shifted outside of the acceptable stress level range. If, in step 413 the stress level of the participant has not deviated from the acceptable stress level range, the algorithm may proceed back to step 409 and continue to collect and monitor the biometric data for indications of stress in the participant. However, if in step 413, the biometric module 127 has determined that the current stress level calculated as a function of the biometric data has deviated from the acceptable stress level range, the algorithm may proceed to step 415.

In step 415 of the algorithm 400, the prediction module 128 of the simulation system 101 may utilize the biometric data collected by the biometrics module 127, and based on the biometric data, the past behaviors of the participant, known behaviors of participants on average and other data collected by the simulation system 101, the prediction module 127 may use machine learning or stochastic simulation to calculate a forward prediction in time of whether or not the stress level deviation identified in step 413 will continue if no modification to the simulation environment is made. If, in step 417 of algorithm 400, it is determined by the prediction module in step 415 that the stress level deviation from the acceptable stress level range will not continue if no modification to the simulation environment is made, then the algorithm 400 may continue to collect and monitor biometric data as described in step 409 above. If, in step 417, a determination is made by the prediction module 128 that the deviation from the acceptable stress level range will continue unless the simulation environment is modified to compensate for the change in stress level of the participant, the algorithm 400 may proceed to step 419 for further action and/or modification to the simulation environment.

In algorithm 400, step 419-423 may describe a computing environment 100 operating in a manual mode as described above, wherein the trainer operating a trainer device 130 may exert additional levels of control over the modification to the simulation environment being implemented by the simulation system 101. In step 419 of algorithm 400, the simulation system 101 may transmit a notification 701 or alert to the trainer device 130. The reporting system 131 of the trainer device 130 may display the notification 701 or alert to the trainer operating the trainer device, as shown in FIG. 7a. The notification 701 may inform the trainer about the type of biometric data being measured that may be considered a deviation from the acceptable stress level range. While operating in manual mode, the trainer may select one or more modification actions 703a, 703b, 703c from the action selection system 135 to implement on the simulation environment.

In step 421, the trainer's selection of one or more modification actions 703a, 703b, 703c from the action selection system 135 may be received by the simulation system 101. The algorithm 400 may proceed to step 423 wherein the scenario module 125 may proceed to apply the modification action(s) 703a, 703b, 703c selected by trainer and received by the simulation system 101 in step 421. Upon application of the modification actions 703a, 703b, 703c, the simulation system 101 may send an updated modification alert 705 to reporting system 131 of the trainer device 130, describing the modifications actions 703a, 703b, 703c implemented and whether or not the modification actions were successful in modifying the simulation environment. Moreover, in some embodiments, the simulation system 101 may send a further notification 707 detailing the success or failure of the modification to re-adjust the participants stress level back within the acceptable stress level range.

Algorithm 500 as shown in FIG. 5, may be an alternative embodiment of algorithm 400 for modifying a simulation. Algorithm 500 may be an algorithm for modifying a simulation while computing environment 100 is operating in semi-automatic mode. Algorithm 500 may incorporate each of the steps 401-417 as described above in algorithm 400. Algorithm 500 may initially start to deviate at step 501 as shown in FIG. 5.

In step 501 of algorithm 500, upon the determination in step 417 that a deviation from the acceptable stress level rage is predicted to continue based on the prediction of step 415, the prediction module 128 may further predict one or more simulation modifications that, if implemented, may correct the stress level deviation and return the stress level of the participant back within the acceptable stress level range. Embodiments of the prediction module 128 may, in some instances use machine learning and/or stochastic simulation to predict the one or more modifications that may have the highest probability of success.

In step 503 of algorithm 500, the simulation system may transmit a notification 801 describing one or more of the simulation modifications identified in step 501 to the trainer device 130. In some embodiments, the notification 801 may describe the deviation from the acceptable stress level range that has been identified and present the most probable or recommended modification to correct the stress level deviation. In alternative embodiments, the notification may give the trainer multiple choices and allow for the trainer to select, using the action selection system 135, the modification preferred by the trainer.

As shown in the exemplary embodiment of FIG. 8a, a trainer operating the trainer device 130 may receive the notification 801 and select whether or not to approve the modification proposed by the simulation system 101 when the simulation system 101 is operating in a semi-automatic mode. The trainer's acceptance or denial of the proposed modification may be transmitted back via network 110 to the simulation system. In step 505 of the algorithm 500, the approved simulation modification of step 503 is received by the simulation system 101 and in step 507, the approved simulation modification is applied to the simulation environment. Similar to the manual operating mode shown in FIG. 7b, in a semi-automatic operating mode, the simulation system may further transmit a modification alert 805 to the trainer device, describing whether or not the modification was successfully applied. Embodiments of the simulation system 101 may also transmit a notification 807 to the trainer device, further reporting the success or failure of the modification applied in step 507 on the stress levels of the participant.

Algorithm 600 may be another alternative embodiment to algorithm 400 and algorithm 500 as described above. Algorithm 600 may be considered an automatic operating mode of computing environment 100, wherein the simulation system 101 predicts, selects and applies a modification to the simulation environment that is predicted to alleviate the deviation from the acceptable stress level range of a simulation participant and return the participant's stress level back within the acceptable stress level range. As shown in FIG. 6, algorithm 600 may incorporate steps 401-417 and step 501 as described above.

Algorithm 600 may deviate from algorithm 500 after step 501 by instead of proceeding to step 503, the algorithm 600 may proceed to step 601, wherein action module 129 of the simulation system 101 may automatically apply the simulation modification predicted in step 501 to correct the deviation of a participant's stress from the acceptable stress level range. Instead of waiting for input from the trainer device as in algorithms 400, 500, algorithm 600 automatically modifies the simulation environment. Based on the predicted modification to be the most suitable or probable to correct the stress levels of the participant, the scenario module 125 may modify the simulation environment automatically, including the modification of one or more adjustable properties of real physical objects 150, virtual objects and/or changes to one or more roles assigned to one or more other participants in the simulation.

In step 603 of the algorithm 600, a notification or alert 901, 903, 905 may be transmitted to the trainer device 130 and/or participant devices 140, describing the types of modifications applied to the simulation environment in step 601. Embodiments of the alert 901, 903, 905 may describe participant and biometric data identified that may have given rise to the stress level deviation to outside of the acceptable stress level range, the modification applied, and the result of the modification on the stress level of the participant(s). As shown in FIG. 9b, the number and types of modifications to the simulation environment may be continuously performed in an effort to correct the stress levels of one or more participants. In the automatic operating mode of algorithm 600, a trainer device 130 and/or participant device 140 may receive multiple alerts 903, 905 throughout the simulation, every time the simulation environment is modified, without any opportunity for the participant and/or trainer to interfere with the modification selections to the simulation scenario.

Computer System

FIG. 10 is a block diagram of internal and external components of a computer system 1000, which may be representative of the one or more computer systems depicted in the computing environment 100 of FIG. 1 and/or the cloud computing environment as shown in FIG. 2, in accordance with the embodiments of the present disclosure. It should be appreciated that FIG. 10 provides only an illustration of one implementation and does not imply any limitations with regard to the environments in which different embodiments may be implemented. In general, the components illustrated in FIG. 10 are representative of any electronic device capable of executing machine-readable program instructions. Examples of computer systems, environments, and/or configurations that may be represented by the components illustrated in FIG. 10 include, but are not limited to, personal computer systems, server computer systems, thin clients, thick clients, laptop computer systems, tablet computer systems, cellular telephones (e.g., smart phones), multiprocessor systems, microprocessor-based systems, network PCs, minicomputer systems, mainframe computer systems, and distributed cloud computing environments that include any of the above systems or devices.

Computer system 1000 may include communications fabric 1002, which provides for communications between one or more processors 103, memory 105, persistent storage 119, communications unit 111, and one or more input/output (I/O) interfaces 113. Communications fabric 1002 can be implemented with any architecture designed for passing data and/or control information between processors (such as microprocessors, communications and network processors, etc.), system memory, peripheral devices, and any other hardware components within a system. For example, communications fabric 1002 can be implemented with one or more buses.

Memory 105 and persistent storage 119 may be computer-readable storage media. Embodiments of memory 105 may include random access memory (RAM) 107 and cache memory 109. In general, memory 105 can include any suitable volatile or non-volatile computer-readable storage media. Software, such as a program 1021 may be stored in persistent storage 119 for execution and/or access by one or more of the respective processors 103 via one or more devices of memory 105. Such software programs 1021 can include a simulation module 121, reporting system 131, 147, scenario selection system 133, action selection system 135, communication delivery system 137 as well as software suitable for the operation of the biometric sensors 141, video system 143, audio system 145, controller 151 and/or communication unit 153.

Persistent storage 119 may include, for example, a plurality of magnetic hard disk drives. Alternatively, or in addition to magnetic hard disk drives, persistent storage 119 can include one or more solid state hard drives, semiconductor storage devices, read-only memories (ROM), erasable programmable read-only memories (EPROM), flash memories, or any other computer-readable storage media that is capable of storing program instructions or digital information. Embodiments of the media used by persistent storage 119 can also be removable. For example, a removable hard drive can be used for persistent storage 119. Other examples include optical and magnetic disks, thumb drives, and smart cards that are inserted into a drive for transfer onto another computer-readable storage medium that is also part of persistent storage 119.

Communications unit 111 provides for communications with other computer systems or devices via a network (e.g., network 110). In this exemplary embodiment, communications unit 111 may include network adapters or interfaces such as a TCP/IP adapter cards, wireless Wi-Fi interface cards, or 3G or 4G wireless interface cards or other wired or wireless communication links. The network can comprise, for example, copper wires, optical fibers, wireless transmission, routers, firewalls, switches, gateway computers and/or edge servers. Software and data used to practice embodiments of the present invention can be downloaded to simulation system 101 or computer system 1000 through communications unit 111 (e.g., via the Internet, a local area network or other wide area network). From communications unit 111, the software and data can be loaded onto persistent storage 119.

One or more I/O interfaces 113 may allow for input and output of data with other devices that may be connected to computer system 1000. For example, I/O interface 113 can provide a connection to one or more external devices 115 such as a keyboard, computer mouse, touch screen, virtual keyboard, touch pad, pointing device, or other human interface devices. External devices 115 can also include portable computer-readable storage media such as, for example, thumb drives, portable optical or magnetic disks, and memory cards. I/O interface 113 may also connect to display 117. Display 117 provides a mechanism to display data to a user and can be, for example, a computer monitor. Display 117 can also be an incorporated display and may function as a touch screen, such as a built-in display of a tablet computer.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising the steps of:
   selecting a simulation scenario comprising a simulation environment and an assigned role to a plurality of participants of the simulation scenario;
   assigning an objective for each of the plurality of participants, wherein said objective includes an acceptable stress level range for each of the plurality of participants;
   receiving biometric data collected by one or more biometric sensors associated with each of the plurality of participants;
   identifying a stress level as a function of the biometric data, associated with a participant selected from the plurality of participants, wherein said stress level is outside of the acceptable stress level range;
   predicting a modification to one or more elements of the simulation environment that would return the stress level of the participant back within the acceptable stress level range;
   applying a stochastic simulation or machine learning to predict an impact of the modification on the stress level of each of the plurality of participants;
   selecting the modification predicted to maintain stress levels of each of the plurality of participants within the acceptable stress level range; and
   applying the modification to one or more elements of the simulation environment in real-time, during commencement of the simulation.

2. The method of claim 1, wherein one or more elements of the simulation environment is selected from the group consisting of a real physical object, a virtual object and a combination thereof, wherein said real physical object and virtual object have one or more adjustable properties.

3. The method of claim 2 wherein the step of applying the modification to the simulation environment alters one or more adjustable properties of the real physical object.

4. The method of claim 1, further comprising the steps of:
   transmitting a request to a computing device requesting application of the modification to the one or more elements of the simulation environment during the commencement of the simulation; and receiving approval from the computing device to apply the modification to the one or more elements of the simulation environment during the commencement of the simulation.

5. The method of claim 1, wherein the one or more biometric sensors collects biometric data selected from the group consisting of heart rate, pulse rate, sweat level, body movement, voice pattern and attentiveness level.

6. The method of claim 1, wherein the step of applying the modification further comprises the steps of:
   altering the assigned role of one or more of the plurality of participants; and
   transmitting a notification to a participant device corresponding to each of the plurality of participants having the assigned role altered.

7. A computer program product comprising:
   one or more computer readable storage media having computer-readable program instructions stored on the one or more computer readable storage media, said program instructions executes a computer-implemented method comprising the steps of:
   selecting a simulation scenario comprising a simulation environment and an assigned role to a plurality of participants of the simulation scenario;
   assigning an objective for each of the plurality of participants, wherein said objective includes an acceptable stress level range calibrated to each of the plurality of participants;
   receiving biometric data collected by one or more biometric sensors associated with each of the plurality of participants;
   identifying a stress level as a function of the biometric data, associated with a participant selected from the plurality of participants, wherein said stress level is outside of the acceptable stress level range;
   predicting, by the processor, a modification to one or more elements of the simulation environment that would alter the stress level of the participant back within the acceptable stress level range;
   applying a stochastic simulation or machine learning to predict an impact of the modification on the stress level of each of the plurality of participants;
   selecting the modification predicted to maintain stress levels of each of the plurality of participants within the acceptable stress level range; and
   applying the modification to one or more elements of the simulation environment in real-time, during commencement of the simulation.

8. The computer program product of claim 7, wherein one or more elements of the simulation environment is selected from the group consisting of a real physical object, a virtual object and a combination thereof, wherein said real physical object and virtual object have one or more adjustable properties.

9. The computer program product of claim 8, wherein the step of applying the modification alters one or more adjustable properties of the real physical object.

10. The computer program product of claim 7, further comprising the steps of:
    transmitting a request to a computing device operated by a trainer, requesting application of the modification to the one or more elements of the simulation environment during the commencement of the simulation; and
    receiving approval from the trainer to apply the modification to the one or more elements of the simulation environment during the commencement of the simulation.

11. The computer program product of claim 7, wherein the one or more biometric sensors collects biometric data selected from the group consisting of heart rate, pulse rate, sweat level, body movement, voice pattern and attentiveness level.

12. A computer system comprising:
    a processor;
    at least one biometric sensor coupled to the processor, the at least one biometric sensor receiving biometric data from a simulation participant;
    a computer-readable storage media coupled to a processor, wherein the computer readable storage media contains program instructions executing a computer-implemented method comprising the steps of:
    selecting a simulation scenario comprising a simulation environment and a role assigned to the simulation participant;
    assigning an objective for the simulation participant, wherein said objective includes an acceptable stress level range calibrated to the simulation participant;
    receiving the biometric data collected by the biometric sensor;
    identifying a stress level as a function of the biometric data, wherein said stress level is outside of the acceptable stress level range;
    predicting a modification to one or more elements of the simulation environment that would alter the stress level of the simulation participant back within the acceptable stress level range;
    applying a stochastic simulation or machine learning to predict an impact of the modification on the stress level of each of the plurality of participants;
    selecting the modification predicted to maintain stress levels of each of the plurality of participants within the acceptable stress level range; and
    applying the modification to one or more elements of the simulation environment in real-time, during commencement of the simulation.

13. The computer system of claim 12, wherein one or more elements of the simulation environment is selected from the group consisting of a real physical object, a virtual object and a combination thereof, wherein said real physical object and virtual object have one or more adjustable properties.

14. The computer system of claim 13, wherein the step of applying the modification alters one or more adjustable properties of the real physical object.

15. The computer system of claim 13, further comprising:
    transmitting a request to a computing device operated by a trainer, requesting application of the modification to the one or more elements of the simulation environment during the commencement of the simulation; and
    receiving approval from the trainer to apply the modification to the one or more elements of the simulation environment during the commencement of the simulation.

16. The computer system of claim 12, wherein the biometric data is selected from the group consisting of heart rate, pulse rate, sweat level, body movement, voice pattern and attentiveness level.

17. The computer system of claim 12, wherein the step of applying the modification further comprises the steps of:
    altering, by the processor, the role assigned to the simulation participant; and transmitting, by the processor, a notification to the simulation participant describing the alteration to the role.

* * * * *